United States Patent [19]
Johnson

[11] Patent Number: 5,569,303
[45] Date of Patent: Oct. 29, 1996

[54] APPARATUS AND METHOD FOR ATTACHING AN OBJECT TO BONE

[76] Inventor: Lanny L. Johnson, 4528 Hagadorn, East Lansing, Mich. 48823

[21] Appl. No.: 324,663

[22] Filed: Oct. 18, 1994

[51] Int. Cl.⁶ .................................................. A61B 17/56
[52] U.S. Cl. .............................. 606/232; 606/72; 606/74
[58] Field of Search .............................. 606/72–75, 232

[56] References Cited

U.S. PATENT DOCUMENTS

| | | | |
|---|---|---|---|
| 1,091,674 | 3/1914 | Lee | 606/72 |
| 2,077,804 | 4/1937 | Morrison | 606/72 |
| 2,485,531 | 10/1949 | Dzus et al. | 606/73 |
| 2,631,584 | 3/1953 | Purificato | 606/73 |
| 4,409,974 | 10/1983 | Freedland | 606/72 |
| 4,498,468 | 2/1985 | Hansson | 606/72 |
| 4,721,103 | 1/1988 | Freedland | 606/72 |
| 5,041,129 | 8/1991 | Hayhurst et al. | 606/232 |
| 5,203,782 | 4/1993 | Gudov et al. | 606/31 |

*Primary Examiner*—Gary Jackson
*Attorney, Agent, or Firm*—Cushman Darby & Cushman

[57] ABSTRACT

A method for attaching an object to bone that includes the steps of preparing an elongated channel in the bone, inserting a fixation device into the channel such that a first axis of the fixation device is generally parallel to the channel, and rotating the fixation device in a rotation plane that is generally parallel to the surface of the bone such that at least a portion of the fixation device is positioned under bone tissue. Fixation devices used in this method include a suture anchor having an elongated body or a dumbbell-shaped body. Another suitable fixation device used has an elongated body including a first side and a second side. A plurality of teeth are provided on the first and second sides and protruding portions extend from a distal end of the body for holding tissue to the bone when the fixation device is rotated within the channel.

16 Claims, 6 Drawing Sheets

APPARATUS AND METHOD FOR ATTACHING AN OBJECT TO BONE

BACKGROUND OF THE INVENTION

1. Field of the Invention

The present invention pertains to an apparatus and method for attaching an object to bone and, in particular, to a fixation device and method for using the fixation device, wherein the device is rotated within an elongated channel formed in a bone such that a portion of the fixation device lies under the bone and objects are attached to the bone using the thus implanted fixation device.

2. Description of the Related Art

A wide variety of devices and methods are known for attaching an object to bone. One such device is disclosed in U.S. Pat. No. 5,041,129, wherein a cylindrical-shaped suture anchor is ejected, end-first, from an insertion tool into a bore formed in a bone. The ends of the suture anchor are beveled and engage the walls of the bore thereby lodging the suture anchor within the bore. The cylindrical-shaped suture anchor has a single suture internally attached to an end of the suture anchor such that the suture extends through a hollow center of the suture anchor. The suture exits from the hollow center at the mid-section of the suture anchor through a channel that extends along the surface of the suture anchor. The suture is used to attach objects to the bone.

This device for affixing an object to bone, however, does not always result in a secure placement of the suture anchor within the bone. The positioning of the suture anchor within the bore is random and depends on such factors as the density of the bone tissue and the presence of bone cavities near the bore. There is no way to precisely control where the cylindrical-shaped suture anchor will engage the walls of the bore after it is ejected from the insertion tool. In addition, if the suture anchor is inserted into a bone comprised mostly of soft tissue, the sharply beveled ends of the suture anchor are likely to cut through the soft tissue when a force is applied to the suture, possibly pulling the anchor out of the bone. Therefore, this device for attaching an object to bone is not suitable for all bone types.

In addition, the suture anchor taught by this patent includes only one suture extending from the mid-section thereof. Because at least two sutures are necessary to tie a ligature, at least two such suture anchors must be implanted into the bone to accomplish this object. Obviously, it is desirable to use as few suture anchors as possible to minimize damage to the patient's tissues.

U.S. Pat. No. 5,203,782 discloses another device for attaching an object to bone. According to this patent, the suture anchor has a spring-shaped elongated body with relatively long legs extending therefrom. The suture anchor is positioned within a bore formed in the bone such that each leg extends in opposite directions parallel to the length of the bore. A suture is attached to the mid-section of the suture anchor such that the suture anchor rotates within the bore when a force is applied to the suture. The legs have sharpened ends that engage the walls of the bore during this rotation. As with the previously described suture anchor device, the positioning of the suture anchor cannot be precisely controlled. The rotation of the suture anchor is random depending on the cavities and softness or density of the bone tissue near the bore. Furthermore, the sharp ends of the legs cut into the soft bone tissue. Therefore, this suture anchor is also not suitable for all types of bones.

SUMMARY OF THE INVENTION

It is an object of the present invention to provide a device and method for attaching an object to bone that overcomes the problems associated with the devices discussed above. In accordance with the principles of the present invention, this objective is achieved by providing a method for attaching an object to bone comprising the steps of preparing an elongated channel within the bone, inserting a fixation device into the channel such that a first axis of the fixation device is generally parallel to the channel, and rotating the fixation device in a rotation plane that is generally parallel to said channel such that at least a portion of the fixation device is positioned under bone tissue.

Suitable fixation devices for use with the above-identified method include a suture anchor having an elongated body, wherein the body is inserted into the channel such that a longitudinal axis of the body extends in the direction of a channel and includes at least one suture receiving passage therethrough extending through a longitudinal axis of the body in the direction generally perpendicular to the longitudinal axis. Other fixation devices include a suture anchor having a generally dumbbell-shaped body, wherein the ends of the body are thicker than the mid-section thereof. A third embodiment for the fixation device includes an elongated body having a first side and a second side, wherein a plurality of teeth are provided on the first and second sides and protruding portions extend from the lowermost surface of the elongated body. Tissue is held between these protruding portions so that it is attached to the bone when the elongated body is rotated within the elongated channel.

These and other objects of the present invention will become apparent during the course of the following detailed description and the appended claims. The invention may best be understood with reference to the accompanying drawings, wherein illustrative embodiments are shown and wherein identical features are labelled with identical reference numerals.

DETAILED DESCRIPTION OF THE PRESENTLY PREFERRED EXEMPLARY EMBODIMENTS

A method of attaching an object to a bone according to the principles of the present invention is described below with reference to FIGS. 1–5.

Figure 1:
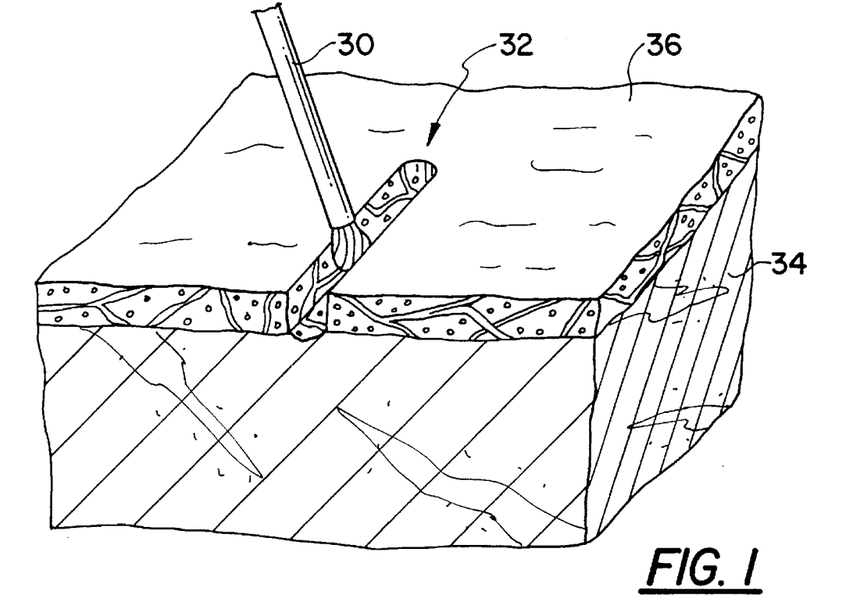
FIG. 1 is a perspective view illustrating a step in preparing an elongated channel in a bone.
Figure 2:
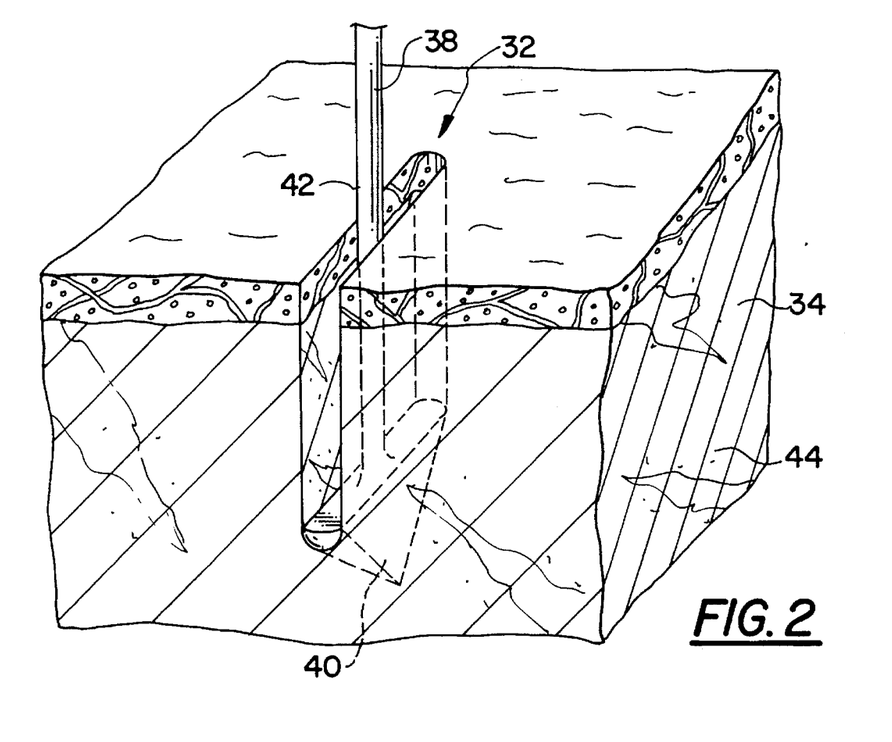
FIG. 2 is a perspective view illustrating another step in preparing an elongated channel in a bone.

First, an elongated channel 32 is formed in bone 34. Forming elongated channel 32 is accomplished by first penetrating the bone surface 36 using, for example, a motorized burr 30 as illustrated in FIG. 1. The size of the channel will depend on such factors as the anatomical size of the bone, the type of fixation device being used, and the location of the insertion site.

Thereafter, a spade 38 is inserted into elongated channel 32 to increase the depth of the elongated channel. See FIG. 2. Spade 38 includes a spade head 40 attached to spade stem 42. Spade head 40 is generally triangular-shaped and has a thickness substantially equivalent to the width of elongated channel 32. The triangular shape of spade head 40 enables spade 38 to easily slice through bone 34 to access the interior 44 of bone 34 until a predetermined depth for elongated channel 32 has been reached. In general, the softer the bone the greater the depth of elongated channel 32 must be to properly implant the fixation device.

Figure 3:
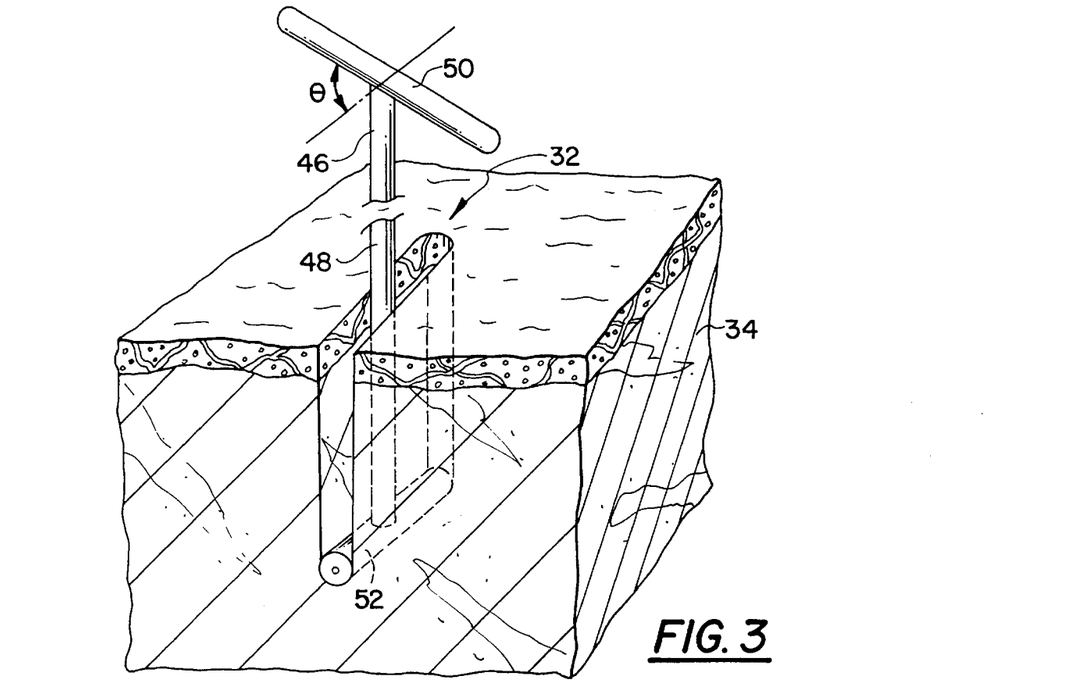
FIG. 3 is a perspective view showing a turn-key device inserted into an elongated channel that is used to form an undercut in the bone.
Figure 4:
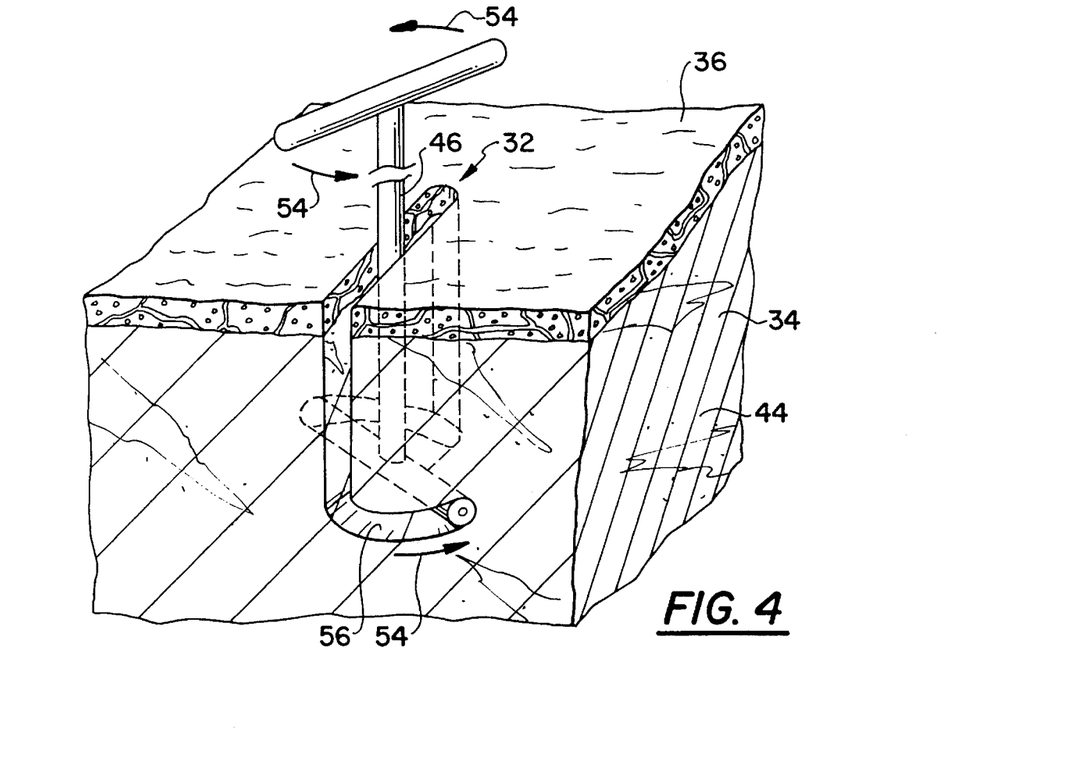
FIG. 4 is perspective view showing the operation of the turn-key device illustrated in FIG. 3.

After the depth of elongated channel 32 has been set using spade 38, a turn-key device 46 is inserted into elongated channel 32. See FIG. 3. Turn-key device 46 includes a turn-key body 48 having a handle 50 attached to the proximal end thereof and turn-key head 52 attached to the distal end thereof. In a preferred embodiment of the present invention, turn-key head 52 is offset from turn-key handle 50 by an angle Θ, which, as illustrated in FIG. 3, is 90 degrees. Turn-key device 46 is rotated in a rotation plane that is generally parallel to bone surface 36, as indicated by arrows 54 in FIG. 4, to form an undercut 56 within the bone interior 44. Because handle 50 is offset from turn-key head 52 by angle Θ, it is easy for a surgeon to determine when the proper amount of rotation has been completed by simply aligning handle 50 with elongated channel 32.

Figure 5:
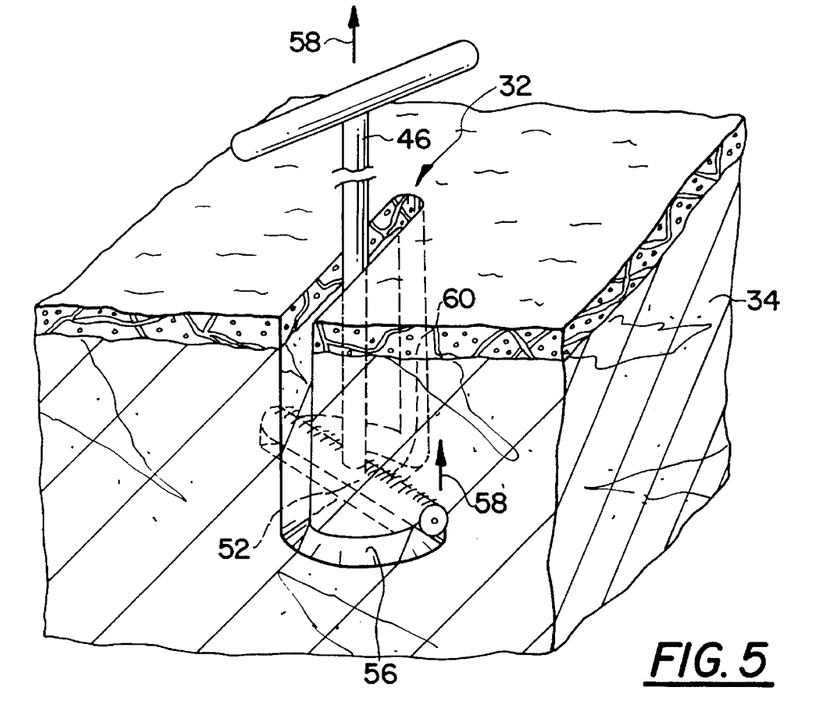
FIG. 5 is a perspective view showing a step of forming compacted bone above the undercut formed by the turn-key device.

Thereafter, a force is applied on turn-key device 46 in the direction indicated by arrow 58 of FIG. 5, which is in a direction generally away from the bone. This force causes turn-key head 52 to compact the bone tissue above the turn-key head thereby forming compacted bone tissue 60 above undercut 56. Compacted bone tissue 60 provides a relatively strong surface that opposes or resists pull-out forces acting on the inserted fixation device. Thus, the fixation device can be implanted even if the bone tissue is relatively soft.

Turn-key device 46 is also useful to test the resistance to pull-out by again applying a force in the direction indicated by arrow 58. If the resistance to pull-out is low, or if the turn-key device pulls out completely, the surgeon will immediately know that the implantation site is poor. This test is particularly important because it allows the surgeon to readily determine the resistiveness of the bone to pull-out forces before a suture has been implanted. In conventional devices, the surgeon could not determine whether the insertion site would be sufficiently resistive to pull-out until the anchoring device was actually implanted.

If the bone is sufficiently resistive to pull-put forces, it is now ready to receive the fixation device adjacent to compacted bone tissue 60.

Figure 6:
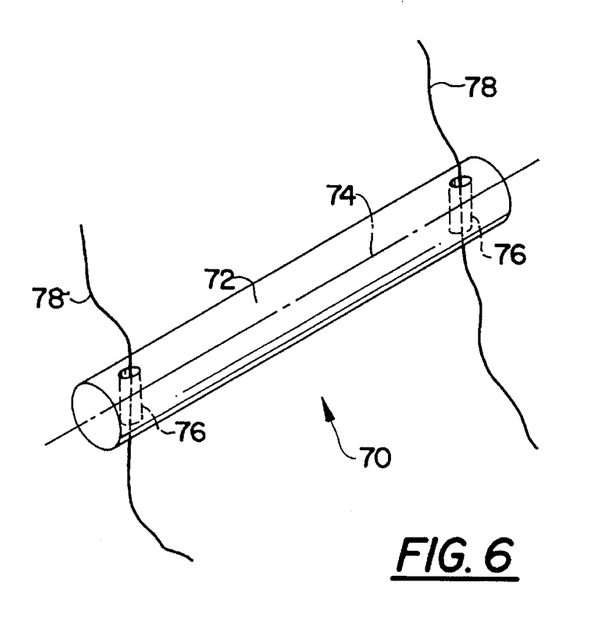
FIG. 6 is a perspective view of a fixation device according to a first embodiment of the present invention.

In a first embodiment of the present invention, the fixation device is a suture anchor, which is generally indicated by 70 in FIG. 6. Suture anchor 70 includes a generally cylindrical-shaped suture anchor body 72 having a longitudinal axis 74. Suture receiving passages 76 are provided through suture anchor body 72 so that sutures 78 can be inserted therethrough. As illustrated in FIG. 6, suture receiving passages 76 extend through longitudinal axis 74 in a direction generally perpendicular to longitudinal axis 74. Suture anchor 70 is suitable for insertion into elongated channel 32 formed by the method illustrated in FIGS. 1–5.

Figure 7:
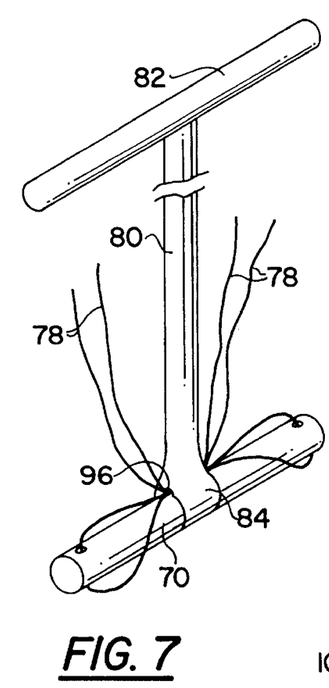
FIG. 7 is a perspective view of a suture anchor insertion tool including the fixation device illustrated in FIG. 6 loaded therein.
Figure 8:
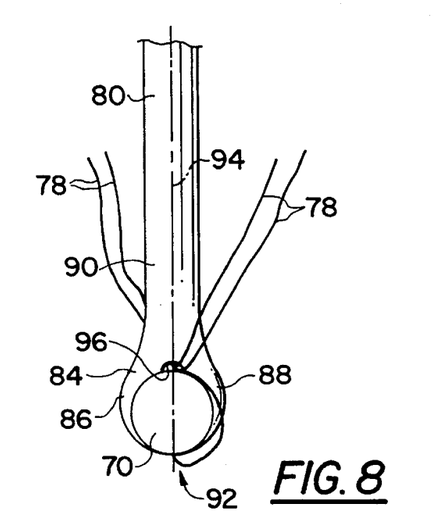
FIG. 8 is a side view of the insertion tool and fixation device illustrated in FIG. 7.

More specifically, suture anchor 70 is inserted into the undercut formed by turn-key device 46 by means of a suture anchor insertion tool 80 illustrated in FIGS. 7 and 8. Suture anchor insertion tool 80 includes a handle 82 at a proximal end thereof and an attaching means 84 for attaching suture anchor 70 to a distal end thereof. A more detailed illustration of attaching means 84 is illustrated in FIG. 8.

Attaching means 84 includes a first prong 86 and a second prong 88 extending from a body 90 of suture anchor insertion tool 80. First and second prongs 86 and 88 define a semicircular channel, generally indicated by 92, at the distal end of insertion tool 80. Semicircular channel 92 extends in a direction generally perpendicular to a longitudinal axis 94 of body 90. First and second prongs 86 and 88 are formed from a semi-flexible material so that suture anchor 70 can be removably held therebetween.

Insertion tool 80 also includes a suture receiving channel 96 located at a crotch defined between first and second prongs 86 and 88. Suture receiving channel 96 enables sutures 78, loaded in suture anchor 70, to be passed between suture anchor 70 and body 90 of insertion tool 80 so that sutures 78 are maintained in a position close to the midsection of suture anchor 70 as the suture anchor is inserted into the bone.

Figure 9:
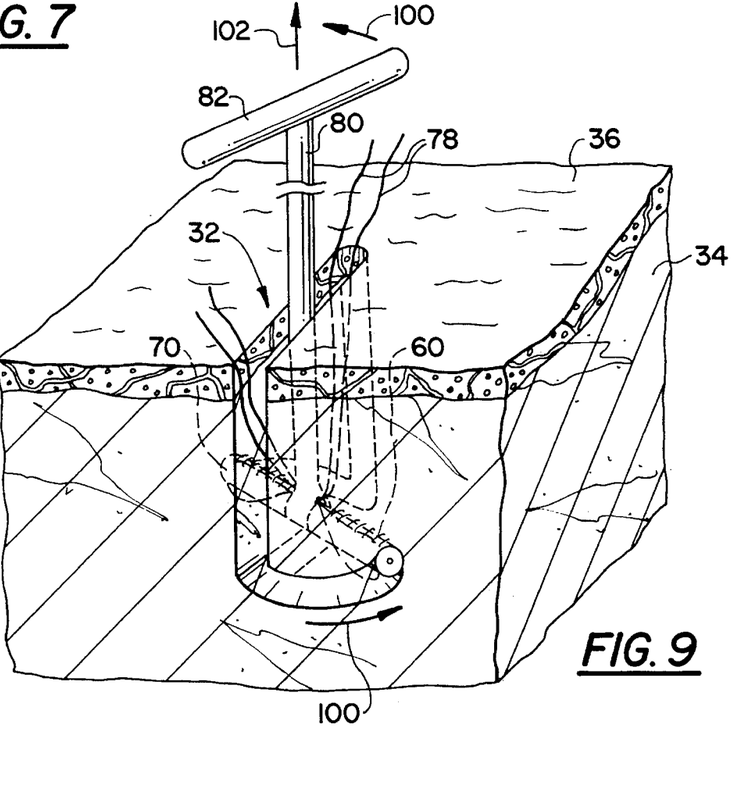
FIG. 9 is perspective view showing the insertion of the fixation device illustrated in FIG. 6 using the insertion tool illustrated in FIGS. 7–8.

FIG. 9 illustrates the method for inserting suture anchor 70 into elongated channel 32 using suture anchor insertion tool 80. Suture anchor 70 is inserted into elongated channel 32 and rotated in a rotation plane that is generally parallel to bone surface 36, as indicated by arrow 100, so that suture anchor 70 lies directly underneath compacted bone 60. Suture anchor insertion tool 80 is then removed from the bone by pulling on handle 82 in a direction indicated by arrow 102. Suture anchor 70 engages compacted bone 60 and detaches from the distal end of suture anchor insertion tool 80 thereby leaving suture anchor 70 within the bone directly underneath compacted bone 60. See FIG. 10.

Figure 10:
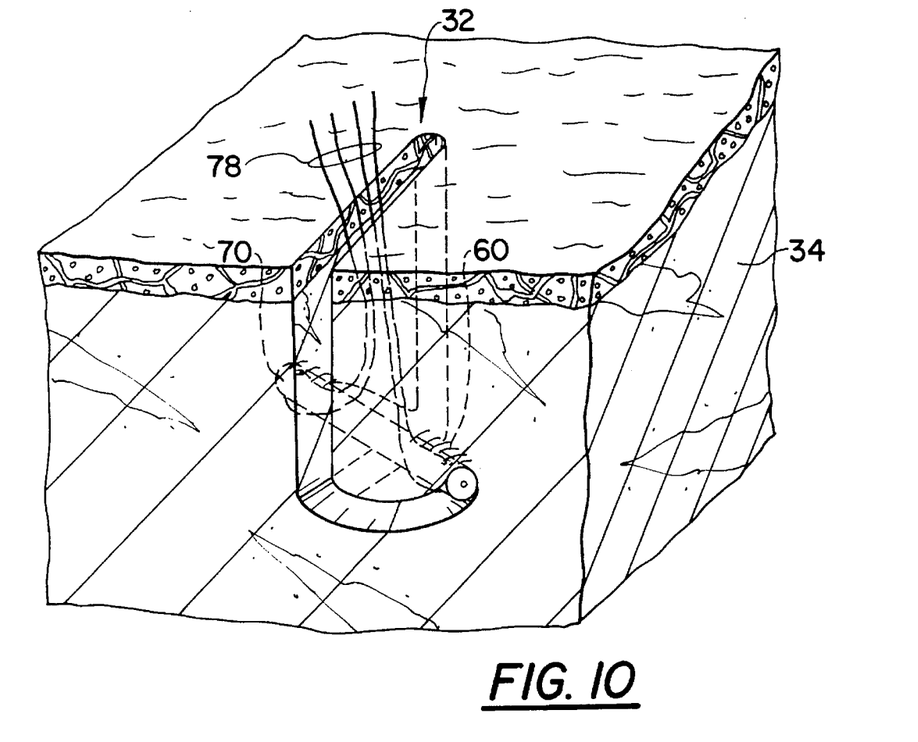
FIG. 10 is perspective view showing the fixation device illustrated in FIG. 6 inserted into a bone.

Sutures 78 extending from elongated channel 32 are used to attach an object to bone 34. Because the present invention includes a plurality of sutures 78, only one insertion site is required to attach an object to the bone. As discussed above, compacted bone tissue 60 is relatively resistive to pull-out by forces tugging on sutures 78, even if the bone is relatively soft. In addition, this method of inserting a fixation device in a bone allows a symmetrical force to be applied to the fixation device to that the forces acting on the device are dispersed along its length.

Figure 11A:
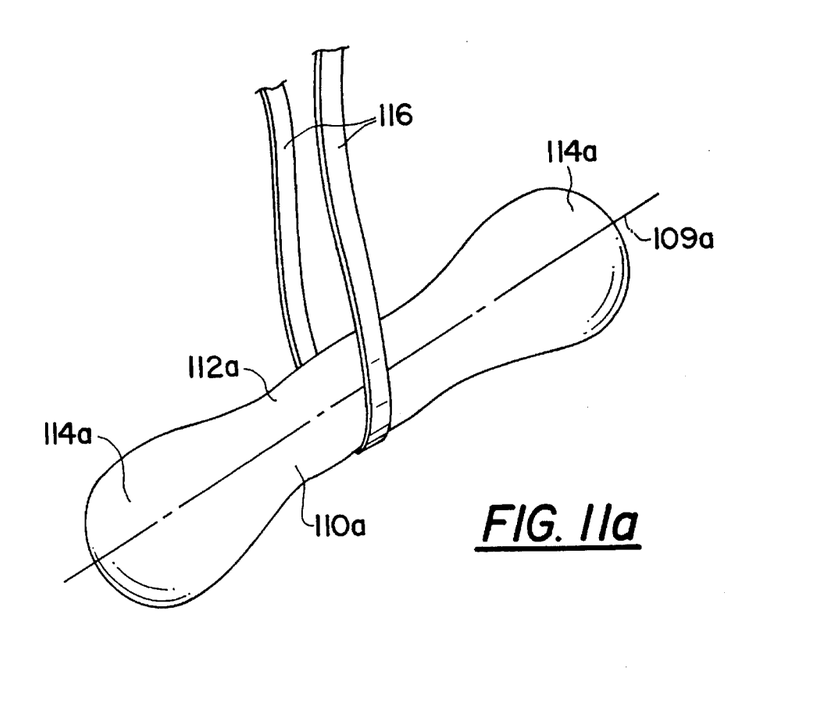
FIGS. 11a and 11b are perspective views of a fixation device according to a second embodiment of the present invention.
Figure 11B:
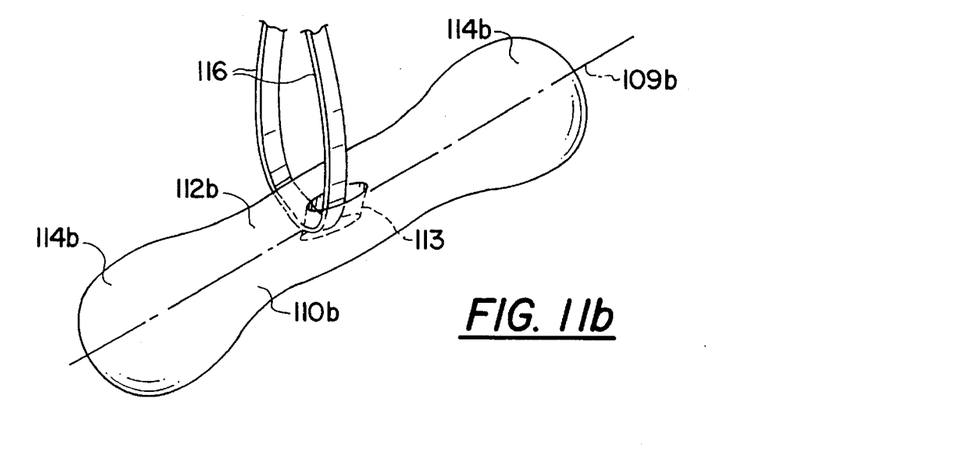

A second embodiment for the suture anchor according to the principles of the present invention is illustrated in FIGS. 11a and 11b. In this embodiment, suture anchor 110a, 110b has a dumbbell-shaped body 112a, 112b, wherein ends 114a, 114b are thicker than a mid-section of body 112a, 112b. As illustrated in FIGS. 11a and 11b, the dumbbell-shaped body gradually tapers outwardly from a longitudinal axis 109a, 109b of body 112a, 112b in a direction away from said mid-section. As illustrated in FIG. 11a, suture 116 is wrapped around the mid-section of dumbbell-shaped body 112a. Because the ends 114a are thicker than the mid-section, suture 116 does not slip over ends 114a of suture anchor 110a thereby retaining suture 116 within the elongated channel. Alternatively, as illustrated in FIG. 11b, suture anchor 110b is inserted through a suture receiving channel 113 through the mid-section of body 112b. It is to be understood that body 112b should be made from a sufficiently strong material and/or suture receiving channel 113 should be small enough so that pull-out forces on suture 116 do not break suture anchor 110b.

Suture anchors 110a and 110b are inserted into an elongated channel formed in a bone as illustrated in FIGS. 1–5 using the insertion tool illustrated in FIGS. 7–9. Therefore, a description of the method for inserting suture anchors 110a and 110b in an elongated channel formed in a bone is omitted.

Figure 12:
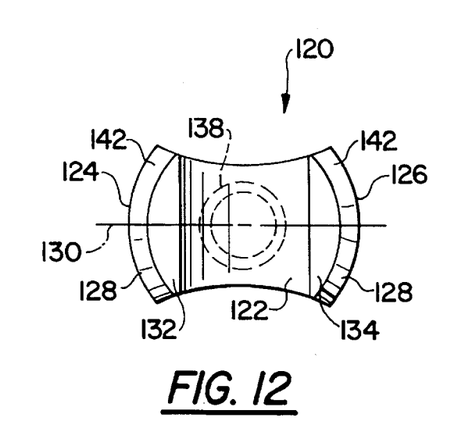
FIG. 12 is a bottom view of a fixation device according to a third embodiment of the present invention.
Figure 13:
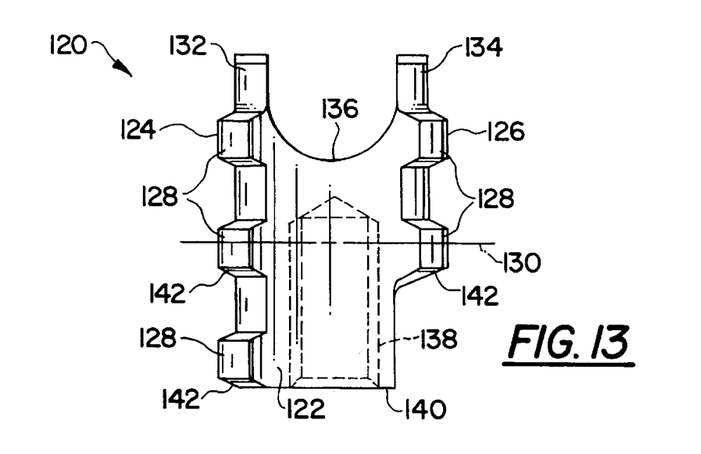
FIG. 13 is a side view of the fixation device illustrated in FIG. 12.

A third embodiment for a fixation device according to the principles of the present invention is illustrated in FIGS. 12–13. The device illustrated in FIGS. 12–13 is specifically suited for attaching ligaments, tendons, or the like, directly to a bone without the use of sutures. As illustrated in FIGS. 12–13, fixation device 120 includes an elongated body 122 having a first side 124 and a second side 126. A plurality of teeth 128 are formed on first and second sides 124 and 126. Teeth 128 extend from elongated body 122 in a direction generally parallel to axis 130. Fixation device 120 includes a first protruding portion 132 and a second protruding portion 134 extending from a distal end of elongated body 122. A crotch 136 is defined between first protruding portion 132 and second protruding portion 134. The tissue to be attached to bone is positioned within crotch 136.

Fixation device 120 is inserted into an elongated slot formed in a bone using the procedures illustrated in FIGS. 1–5. Fixation device 120 is rotated by a device (not shown) inserted into bore 138 so that teeth 128 engage the bone tissue. Proximal surface 140 as well as upper surfaces 142 of the teeth 128 engage the bone tissue to prevent pull-out of fixation device 120. The tissue seated within crotch 136 is securely attached to the bone without the use of sutures or the like.

The tools and fixation devices of the present invention are made from materials that are suitable for insertion into the human body.

It will, thus, be understood that the objects of this invention have fully and effectively accomplished. It should be understood, however, that the foregoing specific embodiments have been shown and described for the purpose of this invention and are subject to change without departure from such principles. Therefore, this invention includes all modifications encompassed within the spirit and scope of the following claims.

What is claimed is:

1. A method for attaching an object to a bone, comprising the steps of:

preparing an elongated channel within said bone;

inserting a fixation device into said channel such that a first axis of said fixation device is generally parallel to said channel, said fixation device including means for attaching said object thereto; and rotating said fixation device in a rotation plane that is generally parallel to the surface of said bone such that at least a portion of said fixation device is positioned under bone tissue.

2. A method for attaching an object to a bone as defined in claim 1, further comprising the steps of:

inserting a turn-key device into said channel before inserting said fixation device in said channel; and rotating said turn-key device in said rotation plane to form an undercut in said bone, wherein said fixation device is positioned within said undercut during said step of rotating said fixation device.

3. A method for attaching an object to a bone as defined in claim 2, further comprising the step of:

applying a force on said turn-key device after rotating said turn-key device, said force being applied in a direction generally away from said bone to compact said bone tissue above said undercut, wherein said fixation device is positioned adjacent to said compacted bone tissue during said step of rotating said fixation device.

4. A method for attaching an object to a bone as defined in claim 1, wherein said fixation device is removably attached to a distal end of a fixation tool, and said step of rotating said fixation device includes rotating a proximal end of said fixation tool thereby rotating said fixation device attached to said distal end of said fixation tool.

5. A method for attaching an object to a bone as defined in claim 1, wherein said step of preparing said elongated channel in said bone includes a step of inserting a spade device into said bone tissue to increase a depth of said elongated channel.

6. A method for attaching an object to a bone as defined in claim 1, wherein said fixation device is a suture anchor having a generally cylindrical-shaped body having a longitudinal axis corresponding to said first axis, said cylindrical-shaped body includes at least one suture receiving passage therethrough, said suture receiving passage extends through said cylindrical-shaped body in a direction generally perpendicular to said longitudinal axis.

7. A method for attaching an object to a bone as defined in claim 6, wherein said suture anchor includes two suture receiving passages symmetrically disposed at each end thereof about a midpoint of said body.

8. A method for attaching an object to a bone as defined in claim 1, wherein said fixation device is a suture anchor having a generally dumbbell-shaped body such that each end of said body is thicker than a mid-section of said body and said first axis corresponding to a longitudinal axis of said dumbbell-shaped body.

9. A method for attaching an object to a bone as defined in claim 1, wherein said fixation device is a tissue anchoring device comprising an elongated body having a first side and a second side, said first side and said second side including at least one tooth extending therefrom in a plane that is generally parallel to said first axis.

10. A method for attaching an object to a bone as defined in claim 9, wherein said means for attaching said object to said fixation device includes two protruding portions extending away from said elongated body in a direction perpendicular to said first axis such that said protruding portions define a crotch therebetween that is suitable for holding said object.

11. A method for attaching an object to a bone as defined in claim 10, wherein said elongated body has a width that is thinner a mid-section thereof than at said first and said second sides.

12. A method for attaching an object to a bone as defined in claim 11, wherein said elongated body includes a bore extending from a proximal surface of said elongated body toward said crotch in a direction generally perpendicular to said first axis.

13. A method for attaching an object to a bone as defined in claim 1, wherein said fixation device is a suture anchor and said step of inserting a fixation device into said channel includes the step of attaching a suture anchor to a distal end of a suture anchor insertion tool, said tool having attaching means for removably attaching said suture anchor to said distal end thereof.

14. A method for attaching an object to a bone as defined in claim 13, further comprising the step of detaching said suture anchor from said suture anchor insertion tool by applying a force on said tool in a direction generally away from said bone so as to remove said suture from said attaching means thereby leaving said suture anchor within said bone.

15. A method for attaching an object to a bone as defined in claim 13, wherein said insertion tool includes a body member having a longitudinal axis and said attaching means includes a first prong and a second prong defining a semi-circular channel in said distal end of said insertion tool, said semi-circular channel extending in a direction generally perpendicular to said longitudinal axis of said body member and being adapted to receive a portion of a body of said suture anchor therein.

16. A method for attaching an object to a bone as defined in claim 15, wherein said insertion tool includes a suture receiving channel disposed at a crotch defined between said first and said second prongs, said suture receiving channel enabling a suture to be passed between said suture anchor and said suture anchor insertion tool when said suture anchor is positioned within said bone.

* * * * *